United States Patent [19]

Storz

[11] Patent Number: 4,608,966

[45] Date of Patent: Sep. 2, 1986

[54] ROD LENS AND ENDOSCOPE INCLUDING THE SAME

[76] Inventor: Karl Storz, Postfach 400, Mittlestrasse 8, Tuttlingen, Fed. Rep. of Germany

[21] Appl. No.: 358,657

[22] Filed: Mar. 16, 1982

[51] Int. Cl.$^4$ ............................................. A61B 1/06
[52] U.S. Cl. ........................................ 128/4; 350/96.26
[58] Field of Search ........................... 128/4, 6–9; 350/96.24, 409, 451, 482, 242, 252, 319, 504, 556, 561, 566, 677

[56] References Cited

U.S. PATENT DOCUMENTS

| | | | |
|---|---|---|---|
| 3,051,166 | 8/1962 | Hounanian | 128/4 |
| 4,076,018 | 2/1978 | Heckele | 128/6 |
| 4,148,551 | 4/1979 | MacAnally | 350/242 |
| 4,360,372 | 11/1982 | Maciejko | 350/96.24 |

*Primary Examiner*—Edward M. Coven
*Assistant Examiner*—Max F. Hindenburg
*Attorney, Agent, or Firm*—Donald D. Mon

[57] ABSTRACT

An endoscope including a rigid tube containing a rod lens, and a lens next to the rod lens cemented to it. Both lenses are embraced by the tube. The risk of destruction of the cement bond joining the lenses is reduced by reducing the diameter of the rod lens along a major portion of its length spaced from the cement bond. The invention includes a rod lens for this use, which has a reduced diameter for the major portion of its length between its ends.

6 Claims, 3 Drawing Figures

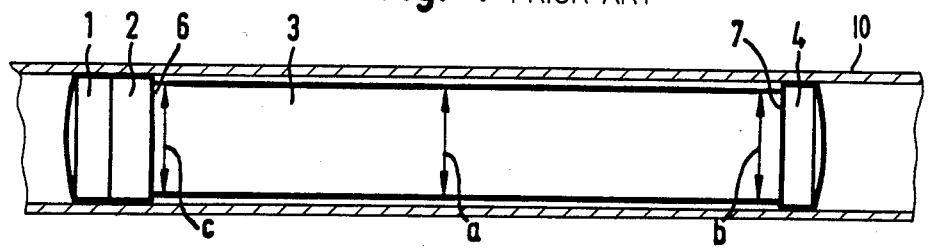
Fig. 1 – PRIOR ART
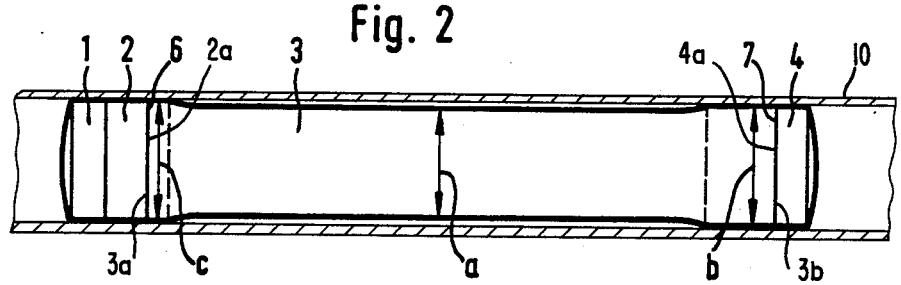
Fig. 2
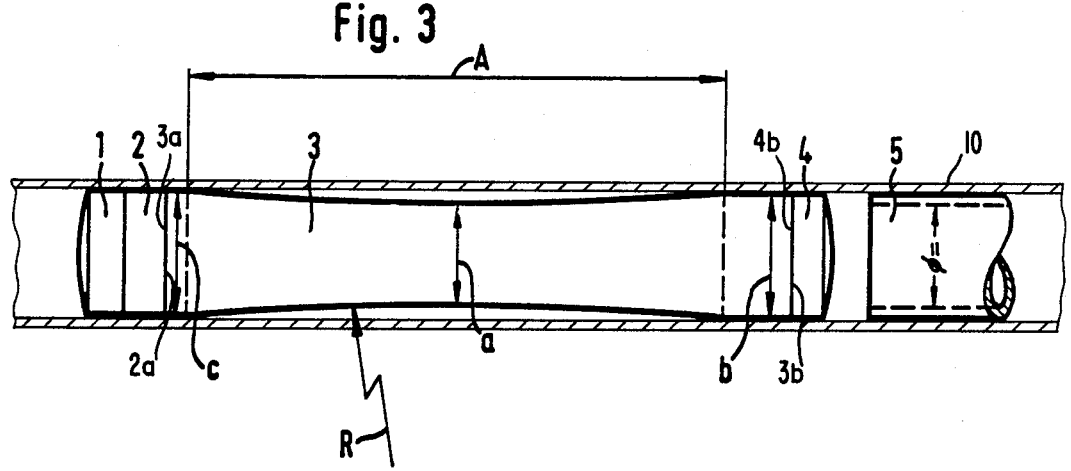
Fig. 3

ROD LENS AND ENDOSCOPE INCLUDING THE SAME

FIELD OF THE INVENTION

The invention relates to a rod lens, particularly for fitting in endoscopes, as well as an arrangement thereof in endoscopes.

BACKGROUND OF THE INVENTION

Due to their small diameter and considerable length there is a risk of endoscope rod lenses shattering. During the handling of medical endoscopes in particular, it is unavoidable that they will be subjected to bending stress, so that shear forces are developed in the center. There is an especial risk to the cement layers used for fixing rod lenses together or fixing rod lenses to normal lenses.

According to the prior art the rod lenses always have a uniform diameter. However, as the ends are cemented to lenses having a larger diameter, an endangered cross-section is formed at this cementing point. If the rod lens arrangement is subject to bending stress within an endoscope, the cement layer may fracture.

The problem of the invention is to so improve the known rod lenses that the cementing points at the ends thereof have a better resistance to shattering than hitherto.

BRIEF SUMMARY OF THE INVENTION

The problem is solved by reducing the outer diameter of the rod lens at its middle, so the outer diameter at its middle is smaller than the outer diameter at its ends. As a result, the ends of the rod lens can have the same diameter as the diameter of an adjacent lens to which the ends are to be cemented. This leads to a much better hold by the endoscope shaft, because in the case of bending stress the two adjacent lenses which are cemented together are equally stressed, whereas hitherto it has been principally the larger diameter lens which has been exposed to the stress.

According to a preferred but optional feature of the invention, the transition of the diameter from the large diameters at the ends, reducing towards the center, is a relatively gradual transition, so that loading peaks and endangered cross-sections are as far as possible avoided.

According to yet another preferred but optional feature of the invention, a spacer sleeve is placed in the endoscope tube between adjacent rod lenses or between groups of lenses that include a rod lens. The spacer sleeves contribute to providing an additional protection against shattering and increase the stability between the individual lenses or lens group.

BRIEF DESCRIPTION OF THE DRAWINGS

The invention is described in greater detail hereinafter relative to non-limitative embodiments and the attached drawings, in which:

FIG. 1 is a side view of an embodiment with several lenses according to the prior art;

FIG. 2 is a side view of a first embodiment according to the invention; and

FIG. 3 is a side view of a second embodiment according to the invention.

DETAILED DESCRIPTION OF THE PREFERRED EMBODIMENTS

FIG. 1 shows a prior art rod lens system, including from left to right lenses 1, 2, 3 and 4, which are cemented to one another. They can in all cases be rod lenses, but lenses 1, 2 and 4 can also be normal lenses. A minimum rod lens system comprises a rod lens portion such as lens 3, and two next lens portions such as lenses 2 and 4.

As can be seen, the diameter of the prior art rod lens 3 is smaller than that of the remaining lenses. According to the prior art this rod lens 3 has a completely uniform diameter a in the center and b and c at the ends. This leads to the disadvantage that even in the case of limited bending of the endoscope, the cement layers 6 and 7 at the ends of lens 3 are highly stressed. This is in particular due to the fact that only lenses 1, 2 and 4 are embraced by the not-shown endoscope shaft, while the outer circumference of the rod lens 3 is not held by the endoscope shaft due to the smaller diameter of lens 3. Thus, in this known arrangement the cement layer 6 and 7 are greatly endangered and fracture easily.

However, according to the embodiment of the invention shown in FIG. 2 the center of rod lens 3 has a smaller diameter a than at its ends b and c. In the vicinity of said ends the diameter is the same as that of the adjacent next lenses 2 on the left and 4 on the right. Thus, in this embodiment, the endangered cement areas at the ends of rod lens 3 are embraced by an endoscope shaft 10 and are also supported by the latter. In the case of a bending stress it is the central area of lens 3 with the smaller diameter a which bends first. The transition from the larger to the smaller diameter is gradual, and in this case is roughly conical. In this area the rod lens is slightly relief-ground.

FIG. 3 shows a further embodiment in which a radius R is provided in the represented manner in the center of region A of the length along rod lens 3. Thus, in this case diameter a is at a minimum in the center.

Here again, the outer ends of rod lens 3 have diameters b and c which coincide with the diameters of lenses 3 and 4 which are cemented to the faces thereof. To the right there is shown a spacer sleeve 5, which can additionally increase the strength of the cemented points.

In this invention, rod lens portion 3 has end faces 3a and 3b. Next lens portions 2 and 4 have respective abutment faces 2a and 4a. Faces 2a and 3a are cemented together, and faces 3b and 4a are cemented together. Each portion has an end region which extends away from its respective face for a substantial distance that has the same diameter as the corresponding end region of the portion to which it is submitted, and these regions are embraced by the inside wall of endoscope tube 10. The reduced diameter of the rod lens portion is small enough that the tube does not contact the central region of the rod lens portion.

Thus, the invention provides a lens arrangement having at least one rod lens, which has a much greater resistance to shattering.

This invention is not to be limited by the embodiments shown in the drawings and described in the description, which are given by way of example and not of limitation, but only in accordance with the scope of the appended claims.

I claim:

1. A rod lens system for close-fitting installation in the inner circularly cylindrical wall of the tube of an endoscope, comprising a rod lens portion, and a pair of next lens portions, said rod lens portion having a pair of end faces, and each said next lens portion having an abutment face, each end face of said rod lens portion having cemented thereto an abutment face of a said next lens portion, each portion having an end region extending for a substantial distance from said faces which has the same diameter as the inside wall of said tube so as to be embraced by it, said rod lens portion having a recessed region between its said end regions which has a diameter that is substantially smaller than the diameter of said end regions, so as not to contact said tube, all cross-sections of all of said lens portions taken normal to said axis being circular, and the length of the rod lens portion being substantially greater than any diameter thereof.

2. A rod lens system according to claim 1 in which said recessed region gradually reduces from said end regions to a smallest section at its mid point.

3. A rod lens system according to claim 1 in which the wall of the recessed region, viewed from the side, lies on a radius whose center is laterally outside of the rod lens portion.

4. A rod lens system according to claim 1 in which the outer wall of the recessed region is a pair of conical frustums which reduce in diameter as they extend away from said end regions.

5. In combination: a rod lens system according to claim 1, and an endoscope tube having a cylindrical inner wall, said rod lenses being held within said inner wall with said inner wall closely embracing all of said end regions.

6. A combination according to claim 5 in which a plurality of said rod lens systems is held in said tube, and in which a spacer is placed between each adjacent pair of rod lens portions.

* * * * *